(12) United States Patent
Aghazadeh

(10) Patent No.: US 9,572,682 B2
(45) Date of Patent: Feb. 21, 2017

(54) SYSTEM AND METHOD FOR PRECISE PROSTHESIS POSITIONING IN HIP ARTHROPLASTY

(71) Applicant: ARTHROMEDA, INC., Ayer, MA (US)

(72) Inventor: Mehran S. Aghazadeh, Newton, MA (US)

(73) Assignee: ARTHROMEDA, INC., Lowell, MA (US)

( * ) Notice: Subject to any disclaimer, the term of this patent is extended or adjusted under 35 U.S.C. 154(b) by 6 days.

(21) Appl. No.: 14/346,632

(22) PCT Filed: Sep. 28, 2012

(86) PCT No.: PCT/US2012/057862
§ 371 (c)(1),
(2) Date: Mar. 21, 2014

(87) PCT Pub. No.: WO2013/049534
PCT Pub. Date: Apr. 4, 2013

(65) Prior Publication Data
US 2014/0330281 A1  Nov. 6, 2014

Related U.S. Application Data

(60) Provisional application No. 61/540,853, filed on Sep. 29, 2011.

(51) Int. Cl.
*A61F 2/46* (2006.01)
*A61B 17/16* (2006.01)
(Continued)

(52) U.S. Cl.
CPC .............. *A61F 2/46* (2013.01); *A61F 2/4607* (2013.01); *A61F 2/4609* (2013.01);
(Continued)

(58) Field of Classification Search
CPC ... A61B 17/56; A61B 2017/564; A61B 17/92; A61B 2017/922; A61B 19/5225; A61F 2/46; A61F 2/4607; A61F 2/4609; A61F 2/4657; A61F 2002/4658; A61F 2002/4668

See application file for complete search history.

(56) References Cited

U.S. PATENT DOCUMENTS 5,007,936 A  4/1991 Woolson
5,527,317 A  6/1996 Ashby et al.
(Continued)

FOREIGN PATENT DOCUMENTS

EP  2358310 A1  8/2011
WO  2012/064513 A1  5/2012

OTHER PUBLICATIONS

Extended European Search Report for Application No. 12835696.1, issued Aug. 3, 2015 (5 pages).
(Continued)

*Primary Examiner* — Larry E Waggle, Jr.
(74) *Attorney, Agent, or Firm* — Nutter McClennen & Fish LLP

(57) ABSTRACT

Provided are systems and methods for precise intra-operative placement and positioning of components of hip prostheses, particularly with respect to avoiding acetabular prosthetic implant malpositioning in the human hip. In one embodiment the system includes at least a pair of electronic sensors as tilt and direction sensors, which are positioned on the patient's native bone structure and the prosthesis, plus at least one of an electronic angle sensor and an electronic leg length measurement unit, plus a computer processor running application software that is capable of receiving and using information from the various electronic sensors to calculate relevant angular relationships and, optionally, distance relationships. The system electronically measures a living sub- (Continued)

A

B

C ject's pelvic tilt and position while lying in the lateral decubitus position during the surgery. The systems and methods provide accurate and precise measurements of the subject's pelvic tilt, angle of inclination, and angle of forward flexion to the surgeon during the procedure by which the hip prosthesis is surgically implanted into the subject.

18 Claims, 8 Drawing Sheets

(51) Int. Cl.
*A61F 2/32* (2006.01)
*A61F 2/34* (2006.01)
*A61F 2/36* (2006.01)
*A61F 2/30* (2006.01)

(52) U.S. Cl.
CPC ........ *A61F 2/4657* (2013.01); *A61B 17/1659* (2013.01); *A61B 17/1668* (2013.01); *A61F 2/32* (2013.01); *A61F 2/34* (2013.01); *A61F 2/36* (2013.01); *A61F 2002/30617* (2013.01); *A61F 2002/4658* (2013.01); *A61F 2002/4668* (2013.01)

(56) References Cited

U.S. PATENT DOCUMENTS

| | | |
|---|---|---|
| 5,652,926 A | 7/1997 | Saito |
| 5,658,294 A | 8/1997 | Sederholm |
| 5,700,268 A | 12/1997 | Bertin |
| 5,737,645 A | 4/1998 | Saito |
| 5,768,134 A | 6/1998 | Swaelens et al. |
| 5,879,402 A | 3/1999 | Lawes et al. |
| 6,027,507 A | 2/2000 | Anderson et al. |
| 6,126,608 A | 10/2000 | Kemme et al. |
| 6,128,445 A | 10/2000 | Nakamura |
| 6,162,191 A | 12/2000 | Foxlin |
| 6,214,014 B1 | 4/2001 | McGann |
| 6,245,109 B1 | 6/2001 | Mendes et al. |
| 6,383,149 B1 | 5/2002 | DeMayo |
| 6,573,706 B2 | 6/2003 | Mendes et al. |
| 6,583,630 B2 | 6/2003 | Mendes et al. |
| 6,685,655 B2 | 2/2004 | DeMayo |
| 6,781,705 B2 | 8/2004 | Waslowski et al. |
| 6,847,435 B2 | 1/2005 | Honda et al. |
| 6,855,118 B2 | 2/2005 | Linton |
| 6,917,827 B2 | 7/2005 | Kienzle, III |
| 6,931,746 B2 | 8/2005 | Pourmanafzadeh |
| 7,022,141 B2 | 4/2006 | Dwyer et al. |
| 7,074,224 B2 | 7/2006 | Daniels et al. |
| 7,372,771 B2 | 5/2008 | Park |
| 7,382,443 B2 | 6/2008 | Ohtomo et al. |
| 7,559,931 B2 | 7/2009 | Stone |
| 7,679,728 B2 | 3/2010 | Kurokawa |
| 7,780,672 B2 | 8/2010 | Metzger et al. |
| 7,854,737 B2 | 12/2010 | Daniels et al. |
| 7,877,131 B2 | 1/2011 | Jansen et al. |
| 7,967,868 B2 | 6/2011 | White et al. |
| 7,981,158 B2 | 7/2011 | Fitz et al. |
| 8,048,167 B2 | 11/2011 | Dietz et al. |
| 8,057,479 B2 | 11/2011 | Stone |
| 8,057,482 B2 | 11/2011 | Stone et al. |
| 8,062,302 B2 | 11/2011 | Lang et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,088,169 B2 | 1/2012 | Dorr et al. |
| 8,092,465 B2 | 1/2012 | Metzger et al. |
| 8,105,330 B2 | 1/2012 | Fitz et al. |
| 8,118,815 B2 | 2/2012 | van der Walt |
| 8,133,234 B2 | 3/2012 | Meridew et al. |
| 8,175,683 B2 | 5/2012 | Roose |
| 8,221,430 B2 | 7/2012 | Park et al. |
| 8,241,293 B2 | 8/2012 | Stone et al. |
| 8,282,646 B2 | 10/2012 | Schoenefeld et al. |
| 8,298,237 B2 | 10/2012 | Schoenefeld et al. |
| 8,337,501 B2 | 12/2012 | Fitz et al. |
| 8,361,163 B2 | 1/2013 | Quaid |
| 8,377,066 B2 | 2/2013 | Katrana et al. |
| 8,390,792 B2 | 3/2013 | Rung et al. |
| 8,398,646 B2 | 3/2013 | Metzger et al. |
| 8,407,067 B2 | 3/2013 | Uthgenannt et al. |
| 8,414,591 B2 | 4/2013 | De Smedt et al. |
| 8,439,978 B2 | 5/2013 | Ebbitt |
| 8,463,577 B2 | 6/2013 | Yuen et al. |
| 8,473,305 B2 | 6/2013 | Belcher et al. |
| 8,480,679 B2 | 7/2013 | Park et al. |
| 8,486,150 B2 | 7/2013 | White et al. |
| 8,500,740 B2 | 8/2013 | Bojarski et al. |
| 8,514,125 B2 | 8/2013 | Van Zeijl et al. |
| 8,514,376 B2 | 8/2013 | D'Aligny et al. |
| 8,529,578 B2 | 9/2013 | Daniels et al. |
| 8,535,387 B2 | 9/2013 | Meridew et al. |
| 8,545,509 B2 | 10/2013 | Park et al. |
| 8,551,099 B2 | 10/2013 | Lang et al. |
| 8,551,169 B2 | 10/2013 | Fitz et al. |
| 8,568,487 B2 | 10/2013 | Witt et al. |
| 8,585,708 B2 | 11/2013 | Fitz et al. |
| 8,588,892 B2 | 11/2013 | Hladio et al. |
| 8,591,516 B2 | 11/2013 | Metzger et al. |
| 8,597,298 B2 | 12/2013 | Daniels et al. |
| 8,603,180 B2 | 12/2013 | White et al. |
| 8,608,748 B2 | 12/2013 | Metzger et al. |
| 8,608,749 B2 | 12/2013 | Meridew et al. |
| 8,611,504 B2 | 12/2013 | Kubiak et al. |
| 8,617,171 B2 | 12/2013 | Park et al. |
| 8,623,026 B2 | 1/2014 | Wong et al. |
| 8,632,547 B2 | 1/2014 | Maxson et al. |
| 8,657,827 B2 | 2/2014 | Fitz et al. |
| 8,696,758 B2 | 4/2014 | Hood et al. |
| 8,702,807 B2 | 4/2014 | Hood et al. |
| 8,705,953 B2 | 4/2014 | Schriefer |
| 8,715,289 B2 | 5/2014 | Smith |
| 8,715,291 B2 | 5/2014 | Park et al. |
| 8,737,700 B2 | 5/2014 | Park et al. |
| 8,777,875 B2 | 7/2014 | Park |
| 8,790,346 B2 | 7/2014 | Daniels et al. |
| 8,801,719 B2 | 8/2014 | Park et al. |
| 8,801,720 B2 | 8/2014 | Park et al. |
| 8,828,087 B2 | 9/2014 | Stone et al. |
| 8,852,188 B2 | 10/2014 | Daniels et al. |
| 8,852,189 B2 | 10/2014 | Daniels et al. |
| 8,852,198 B2 | 10/2014 | De Smedt et al. |
| 8,858,561 B2 | 10/2014 | White et al. |
| 8,861,818 B2 | 10/2014 | Ito et al. |
| 8,864,769 B2 | 10/2014 | Stone et al. |
| 8,868,377 B2 | 10/2014 | Yuen et al. |
| 8,882,779 B2 | 11/2014 | Park et al. |
| 8,888,786 B2 | 11/2014 | Stone et al. |
| 8,900,244 B2 | 12/2014 | Meridew et al. |
| 8,900,246 B2 | 12/2014 | Lashure et al. |
| 8,911,447 B2 | 12/2014 | van der Walt et al. |
| 8,932,299 B2 | 1/2015 | Bono et al. |
| 8,939,982 B2 | 1/2015 | Chellaoui |
| 8,951,259 B2 | 2/2015 | Fitz et al. |
| 8,961,527 B2 | 2/2015 | Park |
| 8,968,320 B2 | 3/2015 | Park et al. |
| 8,974,467 B2 | 3/2015 | Stone |
| 8,974,468 B2 | 3/2015 | Borja |
| 8,979,856 B2 | 3/2015 | Catanzarite et al. |
| 8,979,936 B2 | 3/2015 | White et al. |
| 8,984,731 B2 | 3/2015 | Broeck et al. |
| 8,986,309 B1 | 3/2015 | Murphy |
| 8,998,909 B2 | 4/2015 | Gillman et al. |
| 8,998,910 B2 | 4/2015 | Borja et al. |
| 9,005,297 B2 | 4/2015 | Katrana et al. |
| 9,011,456 B2 | 4/2015 | Ranawat et al. |
| 9,017,337 B2 | 4/2015 | Bartelme et al. |
| 9,020,788 B2 | 4/2015 | Lang et al. |
| 9,023,050 B2 | 5/2015 | Lang et al. |
| 9,072,531 B2 | 7/2015 | Fitz et al. |

(56) References Cited

U.S. PATENT DOCUMENTS

| | | |
|---|---|---|
| 9,084,617 B2 | 7/2015 | Lang et al. |
| 9,107,679 B2 | 8/2015 | Lang et al. |
| 9,107,680 B2 | 8/2015 | Fitz et al. |
| 9,113,823 B2 | 8/2015 | Yuen et al. |
| 9,113,921 B2 | 8/2015 | Lang et al. |
| 9,113,971 B2 | 8/2015 | Metzger et al. |
| 9,121,702 B2 | 9/2015 | Kimura |
| 9,138,258 B2 | 9/2015 | Geebelen |
| 9,138,319 B2 | 9/2015 | Fanson et al. |
| 9,168,103 B2 | 10/2015 | Hladio et al. |
| 9,168,153 B2 | 10/2015 | Bettenga |
| 9,173,661 B2 | 11/2015 | Metzger et al. |
| 9,186,161 B2 | 11/2015 | Lang et al. |
| 9,192,392 B2 | 11/2015 | van der Walt et al. |
| 9,198,760 B2 | 12/2015 | Geebelen |
| 9,204,977 B2 | 12/2015 | Bollinger |
| 9,211,128 B2 | 12/2015 | Gillman et al. |
| 9,241,745 B2 | 1/2016 | Smith et al. |
| 9,265,509 B2 | 2/2016 | Park et al. |
| 9,271,744 B2 | 3/2016 | Meridew |
| 9,289,253 B2 | 3/2016 | Vanasse et al. |
| 9,408,617 B2 | 8/2016 | Ranawat et al. |
| 2002/0077540 A1 | 6/2002 | Kienzle |
| 2005/0148855 A1 | 7/2005 | Kienzle |
| 2006/0190011 A1 | 8/2006 | Ries |
| 2006/0264731 A1 | 11/2006 | Murphy |
| 2008/0021479 A1 | 1/2008 | Penenberg |
| 2008/0257363 A1 | 10/2008 | Schoenefeld et al. |
| 2009/0099570 A1 | 4/2009 | Paradis et al. |
| 2009/0151736 A1 | 6/2009 | Belcher et al. |
| 2009/0318836 A1 | 12/2009 | Stone et al. |
| 2009/0318930 A1 | 12/2009 | Stone et al. |
| 2010/0063509 A1 | 3/2010 | Borja et al. |
| 2010/0076505 A1 | 3/2010 | Borja |
| 2010/0100011 A1 | 4/2010 | Roche |
| 2010/0137871 A1* | 6/2010 | Borja .................. A61F 2/4657 606/91 |
| 2010/0217270 A1 | 8/2010 | Polinski et al. |
| 2010/0274253 A1 | 10/2010 | Ure |
| 2011/0046735 A1 | 2/2011 | Metzger et al. |
| 2011/0092804 A1 | 4/2011 | Schoenefeld et al. |
| 2011/0160736 A1 | 6/2011 | Meridew et al. |
| 2011/0172672 A1 | 7/2011 | Dubeau et al. |
| 2011/0190775 A1 | 8/2011 | Ure |
| 2011/0190899 A1 | 8/2011 | Pierce et al. |
| 2011/0208093 A1 | 8/2011 | Gross et al. |
| 2012/0123423 A1 | 5/2012 | Fryman |
| 2012/0226283 A1 | 9/2012 | Meridew et al. |
| 2012/0245647 A1 | 9/2012 | Kunz et al. |
| 2012/0289965 A1 | 11/2012 | Gelaude et al. |
| 2012/0303004 A1 | 11/2012 | Uthgenannt et al. |
| 2012/0316567 A1 | 12/2012 | Gross et al. |
| 2013/0158671 A1 | 6/2013 | Uthgenannt et al. |
| 2013/0190887 A1 | 7/2013 | Fanson et al. |
| 2013/0197529 A1 | 8/2013 | Metzger et al. |
| 2013/0274633 A1 | 10/2013 | Hladio et al. |
| 2014/0005531 A1 | 1/2014 | Taylor |
| 2014/0018934 A1 | 1/2014 | Meridew et al. |
| 2014/0052149 A1 | 2/2014 | van der Walt et al. |
| 2014/0052270 A1 | 2/2014 | Witt et al. |
| 2014/0074441 A1 | 3/2014 | Fitz et al. |
| 2014/0081275 A1 | 3/2014 | Metzger et al. |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0135658 A1 | 5/2014 | Hladio et al. |
| 2014/0135775 A1 | 5/2014 | Maxson et al. |
| 2014/0135940 A1 | 5/2014 | Goldstein et al. |
| 2014/0275940 A1 | 9/2014 | Hladio et al. |
| 2014/0276867 A1 | 9/2014 | Kelley et al. |
| 2014/0276870 A1 | 9/2014 | Eash |
| 2014/0276871 A1 | 9/2014 | Sherman et al. |
| 2014/0276872 A1 | 9/2014 | Song |
| 2014/0324058 A1 | 10/2014 | Metzger et al. |
| 2014/0336661 A1 | 11/2014 | Stuchin |
| 2014/0364858 A1 | 12/2014 | Li et al. |
| 2014/0378979 A1 | 12/2014 | Stone et al. |
| 2015/0105784 A1 | 4/2015 | Bono et al. |
| 2015/0112348 A1 | 4/2015 | Schoenefeld et al. |
| 2015/0127009 A1 | 5/2015 | Berend et al. |
| 2015/0133945 A1 | 5/2015 | Dushyant et al. |
| 2015/0150569 A1 | 6/2015 | van der Walt et al. |
| 2015/0164657 A1 | 6/2015 | Miles et al. |
| 2015/0182292 A1 | 7/2015 | Hladio et al. |
| 2015/0238204 A1 | 8/2015 | Stone |
| 2015/0238272 A1 | 8/2015 | Ranawat et al. |
| 2015/0272478 A1 | 10/2015 | Borja |
| 2015/0272696 A1 | 10/2015 | Fry et al. |
| 2015/0313684 A1 | 11/2015 | Fanson et al. |
| 2015/0320429 A1 | 11/2015 | Katrana et al. |
| 2015/0320508 A1 | 11/2015 | White et al. |
| 2015/0335438 A1 | 11/2015 | Pierce et al. |
| 2015/0351778 A1 | 12/2015 | Uthgenannt et al. |
| 2016/0008013 A1 | 1/2016 | Metzger et al. |
| 2016/0015466 A1 | 1/2016 | Park et al. |
| 2016/0038160 A1 | 2/2016 | Metzger et al. |
| 2016/0038161 A1 | 2/2016 | Gibson |
| 2016/0038242 A1 | 2/2016 | Lo Iacono et al. |
| 2016/0038307 A1 | 2/2016 | Bettenga |
| 2016/0058577 A1 | 3/2016 | Gillman et al. |
| 2016/0100845 A1 | 4/2016 | Smith et al. |
| 2016/0128706 A1 | 5/2016 | Meridew |
| 2016/0135824 A1 | 5/2016 | Vanasse et al. |

OTHER PUBLICATIONS

International Search Report and Written Opinion for Application No. PCT/US12/57862, issued Dec. 6, 2012 (15 pages).

Drstvensek, I., et al., "Patient Specific Instruments for Total Hip Replacement Surgery," Academic Journal of Manufacturing Engineering, 2013, vol. 11, pp. 6-9.

European Third Party Observation for Application No. 12835696.1, issued Oct. 28, 2016 (5 pages).

* cited by examiner

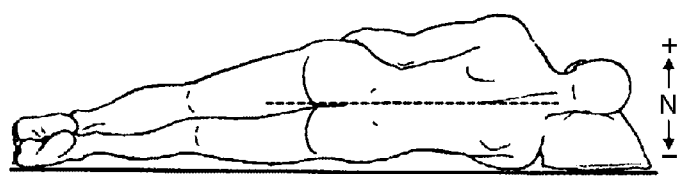 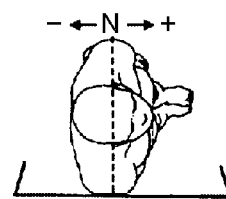
Fig. 4A  Fig. 4B
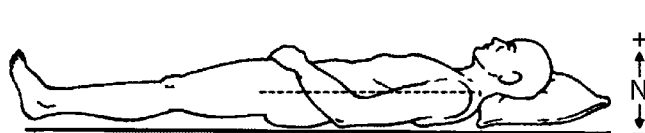 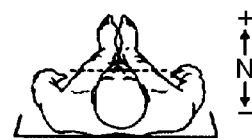
Fig. 4C  Fig. 4D

US 9,572,682 B2

SYSTEM AND METHOD FOR PRECISE PROSTHESIS POSITIONING IN HIP ARTHROPLASTY

RELATED APPLICATION

This application claims benefit under 35 U.S.C. 119(e) of U.S. Provisional Patent Application Ser. No. 61/540,853, filed Sep. 29, 2011.

FIELD OF THE INVENTION

The present invention is concerned generally with devices and surgical techniques for in-vivo implantation of a prosthesis in hip arthroplasty; and is directed specifically to a surgical apparatus, methodology and system for accurate measurement and precise angular placement of a prosthetic implant into the native bone structure of a living host.

BACKGROUND OF THE INVENTION

Joint replacement surgery is a long-established and well accepted mode of treatment for conditions of the human hip, including degenerative arthritis and fracture of the femoral neck. Anatomically, the hip is essentially a ball and socket joint, in which the "ball" or head of the thigh bone (femur) is inserted into and joined with a cup-shaped "socket" in the pelvic bone. Accordingly, when these bones become eroded or broken, a total hip prosthesis is typically surgically implanted to replace the damaged native bone and cartilage within the hip joint.

In essence, a complete hip prosthesis generally comprises four different structural parts, as illustrated by FIG. 1:

(i) an acetabular prosthetic implant (prosthesis), also known as an acetabular "cup" or "shell", that replaces the native acetabulum (hip socket);

(ii) a liner that covers the inner surface of the cup, typically made of polyurethane, ceramic, or metal;

(iii) a metal stem, for insertion into the shaft of the native femur, replacing the femoral neck and providing stability and motion for the reconstructed joint; and (iv) a metal or ceramic ball that replaces the head of the native femur.

In some embodiments parts (iii) and (iv) are provided as a single article of manufacture.

The Recurring Surgical Problem:

Successful hip prosthetic surgery requires precise intraoperative placement and positioning of replacement structures as implants within the host's native bones such that the in vivo function of the reconstructed joint is optimized biomechanically and biologically. For the surgeon, it is necessary to ensure that the replacement structural components are implanted correctly and function in situ properly in order to avoid intra-operative and post-operative complications, as well as to ensure a long-lasting action and use for the implanted prosthesis.

There are three critical parameters for achieving a successful hip arthroplasty procedure: (1) position angles of the cup; (2) position angle of the stem; and (3) longitudinal placement of the stem.

A malpositioned hip prosthesis will not adequately restore the joint's biomechanics, will not function properly, and is at increased risk of intra-operative and post-operative complications. Such complications can include, without limitation, dislocation, impingement, fracture, implant failure, aseptic loosening, subsidence, and even catastrophic outcome. A malpositioned prosthetic implant is particularly susceptible to dislocation and early loosening because the prosthesis will not be well fitted or supported within the host's native bone.

The biggest problem routinely faced by surgeons today concerning human hip replacement procedures is how to achieve proper acetabular prosthetic implant alignment. It is generally agreed among orthopedic surgeons that the ideal anatomic position (for most patients) for positioning the acetabular prosthetic implant within the native bone of the host's hip is at 45° (degrees) of inclination (see below).

A second important angle is the angle of forward flexion (see below), which ideally is at 20° (degrees) of forward flexion. More recent advanced techniques emphasize "combined anteversion" of the reconstructed hip, rather than the cup's absolute angle of forward flexion. Combined anteversion is the sum of the angle of forward flexion of the cup plus the angle of anteversion of the stem. Since there is limited space for changing the stem's angle of anteversion, adjusting the position of the cup to that of the stem is critical to improving stability of the reconstructed hip and reducing impingement.

However, precise measurement of these specific angles, and therefore proper placement of the prostheses, has been difficult to achieve, mostly because two of these angles are relative to the patient's pelvis and the patient is covered by sterile surgical drapes during the course of the hip replacement operation. It also has not been possible to monitor any change in position of the patient's pelvis that can occur after draping the patient for the surgery.

Besides the implants' angles, tension of the soft tissue surrounding the hip is another important factor in stability of the reconstructed joint. The common tendency is adding to the length or offset of the limb to make the joint stable. In many cases the soft tissue is not tight enough to provide adequate stability and allow the most suitable prosthesis with adequate length to be implanted. It is very important to be aware of amount of change in length of the leg intra-operatively to achieve a balance between leg length and offset and avoid changes in leg length more or less than what intended.

It is also critical to realize that almost all patients with arthritic and broken hips have different degrees of shortening of the leg pre-operatively, causing leg length inequality. A common expectation, at least as important as replacement of the damaged joint, is correction of this discrepancy. Following total hip arthroplasty, otherwise satisfactory clinical results can be undermined by dissatisfaction related to a change in leg length. Moreover, leg length discrepancy after total hip arthroplasty has been reported to be associated with inferior clinical outcome.

Currently there is no device to accurately measure the change in length of the leg caused by the operation. This causes another common problem with the biggest impact on patient's satisfaction, the discrepancy between length of the operative and non-operative legs.

Currently Available Surgical Options and Choices:

It is therefore somewhat surprising to recognize that conventionally available modes of avoiding malpositioned prosthetic implants remain relatively few in number. All of these currently available techniques are cumbersome, intricate and/or complex. A summary review of the presently available options is presented below.

(1) One method to facilitate insertion of an acetabular prosthetic implant is to use a visual alignment guide device that attaches to an acetabular cup impactor (a tool used to hammer a prosthetic cup into place). Once attached, the alignment guide device provides a point of reference for the operating table and the topographical surface upon which the patient rests. See FIGS. 2A and 2B.

When using this particular technique, the surgeon must assume that the patient's body lies parallel, and the pelvis lies perpendicular, to the operating table surface. The surgeon must further assume that the surface of the operating table itself is parallel to the operating room floor and the floor itself is horizontal. Based upon these assumptions, the alignment guide device is then also presumed to be parallel to the floor during the time the surgeon implants the prosthesis.

Nevertheless, the surgeon often discovers that the underlying assumptions for using the alignment guide device are false and ultimately finds that the resultant angle of inclination for the prosthetic implant is often quite different from what was expected. Thus, even when this procedure has been correctly utilized, it is not unusual for the surgeon to see a post-operative x-ray which depicts an acetabular prosthetic implant in less than an ideal aligned position, with either a markedly increased or greatly decreased angle of inclination and/or angle of forward flexion. The other underlying problem with such conventional alignment guide devices is that the measurements are only subjective, i.e., they do not have any calibrated component by which to measure the angles of inclination or forward flexion in situ.

(2) Surgeons are commonly aware that acetabular prosthetic implant malpositioning is often caused by an unrecognized/undiscovered tilting of the host's pelvis which occurs after the patient is placed in the lateral decubitus position (i.e., lying on the side of the body) for the surgery. This recognition and awareness has persuaded some surgeons to use intra-operative x-rays as a means for detecting pelvic tilt, which may occur at any time during the course of the surgical operation, and evaluating position of the acetabular implant.

However, there are multiple disadvantages in following this procedure, among which are the following: This intra-operative x-ray technique is frequently very time-consuming and can potentially increase the risk of infection owing to the introduction of non-sterile x-ray equipment into the operating theater. In addition, the obtained x-ray images (which are directed antero-posteriorly through the host's pelvis) are almost invariably of poor quality; and useful bony landmarks (such as the anterior superior iliac spine) are often obscured within the x-ray image. These obstacles and disadvantages markedly hinder the surgeon's ability to detect or accurately measure the degree of pelvic tilt.

Furthermore, the surgeon would be required to break sterile scrub in order to use a computer to detect digitally the existence and degree of pelvic tilt and implant angle. Moreover, even if a particular degree of pelvic tilt were discovered during the operation, there is no way for the surgeon to adjust the alignment of the prosthesis with the same accuracy and precision as the measurement made using computerized digital tools.

Thus, even if intra-operative x-rays were used to determine the existence and degree of pelvic tilt, this measurement would only be of limited assistance in determining the proper inclination of the acetabular implant and would not help in any meaningful way in determining the proper degree of inclination/forward flexion for the acetabular component. In effect, assessing the presence of any changes in patient pelvic tilt or cup position would require the taking and evaluation of ever more x-ray images.

(3) The intra-operative estimation of anteversion of the femoral component of a total hip arthroplasty is generally made by the surgeon's visual assessment of the stem position relative to the condylar plane of the femur. Although the generally accepted range of intended anteversion is between 10° and 20°, the surgeon's estimation of the anteversion of the femoral stem has poor precision and is often not within the intended range of 10° to 20° of anteversion. Alternatively, modular femoral components or stems with retroverted or anteverted necks could be used, but these components are much more expensive than non-modular femoral stems.

(4) Computerized navigation systems are recognized today as being useful tools for aiding with acetabular implant position. Nevertheless, the computerized navigation system itself is very expensive equipment; and it requires both a pre-operative CT (computerized tomography) scan and time-consuming pre-operative planning in order to be used effectively during the surgery.

In particular, intra-operative positioning of the digitizing frames is time-consuming and requires the placement of pins and numerous surgical incisions. Also registration with digitizing probes is very time-consuming; and this technique is always vulnerable to an unexpected software or hardware failure, which is not immediately replaceable in many instances.

Also, loosening of the implanted pins, especially in older and osteoporotic patients, is always a risk. The main risk factor is their location (inside the operating field) that leaves them at risk of getting accidentally jarred. In addition, being in the surgical field is another reason that makes computerized navigation undesirable for many surgeons since it limits the surgical field. Thus, more surgeons than ever before are still looking for an alternative and better method, especially after encountering the difficulties imposed by the computerized navigation guided system on multiple surgical occasions.

(5) Still other surgeons follow a specific and routine practice as a mode of quality control. Such surgeons consistently and invariably insert the acetabular component in the host at 35° of inclination, even though the proper goal is placement at an angle of 45°. Their rationale is simple: It is impossible to know whether or not the host's pelvis has become tilted during the surgery. Accordingly, it is anatomically better to achieve a cup position having a less-than-perfect angle of inclination, but with certainty, rather than involuntarily create too large an angle of inclination for the implanted prosthesis. In short, these surgeons knowingly preferred to err with certainty rather than with uncertainty.

SUMMARY OF THE INVENTION

An aspect of the invention is a system for use in performing hip arthroplasty. The system includes:

a computer processor;

an axis guide, comprising a substantially linear rigid bar at least as long as a human subject's pelvis is wide, constructed and arranged to have a slot at each end of the bar and at least two apertures adjacent and perpendicular to at least one of the slots, wherein each of the apertures is capable of receiving a pin guide and each pin guide is capable of receiving a securing pin; a first electronic position sensor (ES1) capable of reporting information about its orientation in 3-dimensional space to the computer processor;

a second electronic position sensor (ES2) capable of reporting information about its orientation in 3-dimensional space to the computer processor;

an electronic angle sensor (AS) comprising an electronic angle sensor device connected via a pivot point to each of two rotatable arms, the first arm constructed and arranged to be inserted into a femoral neck, attached to a broach handle, or attached to a femoral stem, and the second arm comprising a light pointer aligned parallel to the long axis of said second arm, wherein the electronic angle sensor device is capable of reporting information about angular relationship between the arms to the computer processor; and application software capable of (i) receiving information from the first electronic position sensor (ES1), the second electronic position sensor (ES2), and the electronic angle sensor (AS); and (ii) calculating and causing to be displayed angular relationships derived from the position and angle sensor information.

In one embodiment, the system further includes an electronic visual display connected to the computer processor, wherein the visual display is capable of displaying the calculated angular relationships.

In one embodiment, at least one of the first electronic position sensor, the second electronic position sensor, and the electronic angle sensor is capable of communicating wirelessly with the computer processor. In one embodiment, each of the first electronic position sensor, the second electronic position sensor, and the electronic angle sensor is capable of communicating wirelessly with the computer processor.

In one embodiment, the angular relationships comprise any one or more of: (pelvic) axial tilt, (pelvic) anterior-posterior (AP) tilt, absolute angle of inclination, absolute angle of forward flexion, true angle of inclination, and true angle of forward flexion.

In one embodiment the angular relationships comprise each of: (pelvic) axial tilt, (pelvic) anterior-posterior (AP) tilt, absolute angle of inclination, absolute angle of forward flexion, true angle of inclination, and true angle of forward flexion.

In one embodiment, the calculating is performed on demand.

In one embodiment, the calculating is performed continuously in real time.

In one embodiment, the system further includes the at least two pin guides.

In one embodiment, the system further includes the at least two securing pins.

An aspect of the invention is a system for use in performing hip arthroplasty. The system includes:

a computer processor;

an axis guide, comprising a substantially linear rigid bar at least as long as a human subject's pelvis is wide, constructed and arranged to have a slot at each end of the bar and at least two apertures adjacent and perpendicular to at least one of the slots, wherein each of the apertures is capable of receiving a pin guide and each pin guide is capable of receiving a securing pin;

a first electronic position sensor (ES1) capable of reporting information about its orientation in 3-dimensional space to the computer processor;

a second electronic position sensor (ES2) capable of reporting information about its orientation in 3-dimensional space to the computer processor;

a leg length measurement unit, comprising (i) a substantially planar bracket constructed and arranged to receive at least two securing pins spaced and oriented in accordance with the apertures of the axis guide; (ii) a reflection pin; and (iii) an electronic distance sensor (DS) capable of being attached to the bracket and capable of reporting, to the computer processor, information about its distance from the reflection pin; and application software capable of (i) receiving information from the first electronic position sensor (ES1), the second electronic position sensor (ES2), and the electronic distance sensor (DS); (ii) calculating and causing to be displayed angular relationships derived from the position sensor information; and (iii) calculating and causing to be displayed leg length information derived from the distance sensor information.

In one embodiment, the system further includes an electronic visual display connected to the computer processor, wherein the visual display is capable of displaying the calculated angular relationships and leg length information.

In one embodiment, at least one of the first electronic position sensor, the second electronic position sensor, and the electronic distance sensor is capable of communicating wirelessly with the computer processor. In one embodiment, each of the first electronic position sensor, the second electronic position sensor, and the electronic distance sensor is capable of communicating wirelessly with the computer processor.

In one embodiment, the angular relationships comprise any one or more of: absolute angle of inclination, absolute angle of forward flexion, true angle of inclination, and true angle of forward flexion.

In one embodiment, the angular relationships comprise each of: absolute angle of inclination, absolute angle of forward flexion, true angle of inclination, and true angle of forward flexion.

In one embodiment, the calculating is performed on demand.

In one embodiment, the calculating is performed continuously in real time.

In one embodiment, the system further includes the at least two pin guides.

In one embodiment, the system further includes the at least two securing pins.

In one embodiment, the substantially planar bracket of the leg length measurement unit is a diapason (tuning fork)-shaped bracket having two fork ends and one handle end, wherein each of the two fork ends comprises a hole constructed and arranged to accept an exposed end of a securing pin, and the handle end is constructed and arranged to attach to the electronic distance sensor (DS).

An aspect of the invention is a system for use in performing hip arthroplasty. The system includes:

a computer processor;

an axis guide, comprising a substantially linear rigid bar at least as long as a human subject's pelvis is wide, constructed and arranged to have a slot at each end of the bar and at least two apertures adjacent and perpendicular to at least one of the slots, wherein each of the apertures is capable of receiving a pin guide and each pin guide is capable of receiving a securing pin;

a first electronic position sensor (ES1) capable of reporting information about its orientation in 3-dimensional space to the computer processor;

a second electronic position sensor (ES2) capable of reporting information about its orientation in 3-dimensional space to the computer processor;

an electronic angle sensor (AS) comprising an electronic angle sensor device connected via a pivot point to each of two rotatable arms, the first arm constructed and arranged to be inserted into a femoral neck, attached to a broach handle, or attached to a femoral stem, and the second arm comprising a light pointer aligned parallel to the long axis of said second arm, wherein the electronic angle sensor device is capable of reporting information about angular relationship between the arms to the computer processor;

a leg length measurement unit, comprising (i) a substantially planar bracket constructed and arranged to receive at least two securing pins spaced and oriented in accordance with the apertures of the axis guide; (ii) a reflection pin; and (iii) an electronic distance sensor (DS) capable of being attached to the bracket and capable of reporting, to the computer processor, information about its distance from the reflection pin; and application software capable of (i) receiving information from the first electronic position sensor (ES1), the second electronic position sensor (ES2), the electronic angle sensor (AS), and the electronic distance sensor (DS); (ii) calculating and causing to be displayed angular relationships derived from the position and angle sensor information; and (iii) calculating and causing to be displayed leg length derived from the distance sensor information.

In one embodiment, the system further includes an electronic visual display connected to the computer processor, wherein the visual display is capable of displaying the calculated angular relationships.

In one embodiment, at least one of the first electronic position sensor, the second electronic position sensor, the electronic angle sensor, and the electronic distance sensor is capable of communicating wirelessly with the computer processor. In one embodiment, each of the first electronic position sensor, the second electronic position sensor, the electronic angle sensor, and the electronic distance sensor is capable of communicating wirelessly with the computer processor.

In one embodiment, the angular relationships comprise any one or more of: (pelvic) axial tilt, (pelvic) anterior-posterior (AP) tilt, absolute angle of inclination, absolute angle of forward flexion, true angle of inclination, and true angle of forward flexion.

In one embodiment, the angular relationships comprise each of: (pelvic) axial tilt, (pelvic) anterior-posterior (AP) tilt, absolute angle of inclination, absolute angle of forward flexion, true angle of inclination, and true angle of forward flexion.

In one embodiment, the calculating is performed on demand.

In one embodiment, the calculating is performed continuously in real time.

In one embodiment, the system further includes the at least two pin guides.

In one embodiment, the system further includes the at least two securing pins.

In one embodiment, the substantially planar bracket of the leg length measurement unit is a diapason (tuning fork)-shaped bracket having two fork ends and one handle end, wherein each of the two fork ends comprises a hole constructed and arranged to accept an exposed end of a securing pin, and the handle end is constructed and arranged to attach to the electronic distance sensor (DS).

An aspect of the invention is a method for precise intra-operative positioning of a total hip prosthesis in a human subject. The method includes the steps of:

determining the pelvic axis of a human subject in need of hip arthroplasty;

attaching a first electronic position sensor (ES1) to a bony anatomic site on the pelvic axis of the subject;

attaching a second electronic position sensor (ES2) to a cup impactor, wherein the first and second electronic position sensors are capable of acting in combination to report information useful to calculate the true angle of inclination and the true angle of forward flexion of the acetabular prosthetic cup;

contacting the cup impactor with an acetabular prosthetic cup that is to be implanted into the prosthetic implantation site in the patient;

attaching an electronic angle sensor to a structure selected from the group selected from native femoral neck, prosthetic femoral stem, and broach handle, wherein the electronic angle sensor is capable of reporting information useful to calculate the angle of anteversion of the structure to which it is attached;

transferring information from the first and second electronic position sensors to a computer processor running application software, wherein the application software calculates the true angle of inclination and the true angle of forward flexion of the acetabular prosthetic cup;

transferring information from the electronic angle sensor to the computer processor running application software, wherein the application software calculates the angle of anteversion of the structure to which it is attached; and displaying results of the calculations on an electronic visual display device while the prosthesis is being surgically positioned for implantation into the subject.

In one embodiment, the calculated measurements are displayed on demand.

In one embodiment, the calculated measurements are displayed continuously.

An aspect of the invention is a method for precise intra-operative positioning of a total hip prosthesis in a human subject. The method includes the steps of:

determining the pelvic axis of a human subject in need of hip arthroplasty;

attaching a first electronic position sensor (ES1) to a bony anatomic site on the pelvic axis of the subject;

attaching a second electronic position sensor (ES2) to a cup impactor, wherein the first and second electronic position sensors are capable of acting in combination to report information useful to calculate the true angle of inclination and the true angle of forward flexion of the acetabular prosthetic cup;

contacting the cup impactor with an acetabular prosthetic cup that is to be implanted into the prosthetic implantation site in the patient;

attaching an electronic leg length measurement unit, comprising (i) a substantially planar bracket constructed and arranged to receive at least two securing pins spaced and oriented in accordance with the apertures of the axis guide; (ii) a reflection pin; and (iii) an electronic distance sensor (DS) capable of being attached to the bracket and capable of reporting, to the computer processor, information about its distance from the reflection pin;

transferring information from the first and second electronic position sensors to a computer processor running application software, wherein the application software calculates the true angle of inclination and the true angle of forward flexion of the acetabular prosthetic cup;

transferring information from the electronic distance sensor to the computer processor running the application software, wherein the application software calculates the distance between the distance sensor and the reflecting pin; and displaying results of the calculations on an electronic visual display device while the prosthesis is being surgically positioned for implantation into the subject.

In one embodiment, the calculated measurements are displayed on demand.

In one embodiment, the calculated measurements are displayed continuously.

An aspect of the invention is a method for precise intra-operative positioning of a total hip prosthesis in a human subject. The method includes the steps of:

determining the pelvic axis of a human subject in need of hip arthroplasty;

attaching a first electronic position sensor (ES1) to a bony anatomic site on the pelvic axis of the subject;

attaching a second electronic position sensor (ES2) to a cup impactor, wherein the first and second electronic position sensors are capable of acting in combination to report information useful to calculate the true angle of inclination and the true angle of forward flexion of the acetabular prosthetic cup;

contacting the cup impactor with an acetabular prosthetic cup that is to be implanted into the prosthetic implantation site in the patient;

attaching an electronic angle sensor to a structure selected from the group selected from native femoral neck, prosthetic femoral stem, and broach handle, wherein the electronic angle sensor is capable of reporting information useful to calculate the angle of anteversion of the structure to which it is attached;

attaching an electronic leg length measurement unit, comprising (i) a substantially planar bracket constructed and arranged to receive at least two securing pins spaced and oriented in accordance with the apertures of the axis guide; (ii) a reflection pin; and (iii) an electronic distance sensor (DS) capable of being attached to the bracket and capable of reporting, to the computer processor, information about its distance from the reflection pin;

transferring information from the first and second electronic position sensors to a computer processor running application software, wherein the application software calculates the true angle of inclination and the true angle of forward flexion of the acetabular prosthetic cup;

transferring information from the electronic angle sensor to the computer processor running application software, wherein the application software calculates the angle of anteversion of the structure to which it is attached;

transferring information from the electronic distance sensor to the computer processor running the application software, wherein the application software calculates the distance between the distance sensor and the reflecting pin; and displaying results of the calculations on an electronic visual display device while the prosthesis is being surgically positioned for implantation into the subject.

In one embodiment, the calculated measurements are displayed on demand.

In one embodiment, the calculated measurements are displayed continuously.

BRIEF DESCRIPTION OF THE FIGURES

The present invention can be more easily understood and better appreciated when taken in conjunction with the accompanying drawings, in which:

FIG. 4A depicts axial tilt when a subject is in lateral decubitus position. N, neutral; +, positive; −, negative.

FIG. 4B depicts anterior-posterior (AP) tilt when a subject is in lateral decubitus position. N, neutral; +, positive; −, negative.

FIG. 4C depicts axial tilt when a subject is in supine position. N, neutral; +, positive; −, negative.

FIG. 4D depicts AP tilt when a subject is in supine position. N, neutral; +, positive; −, negative.

DETAILED DESCRIPTION OF THE INVENTION

Figure 1:
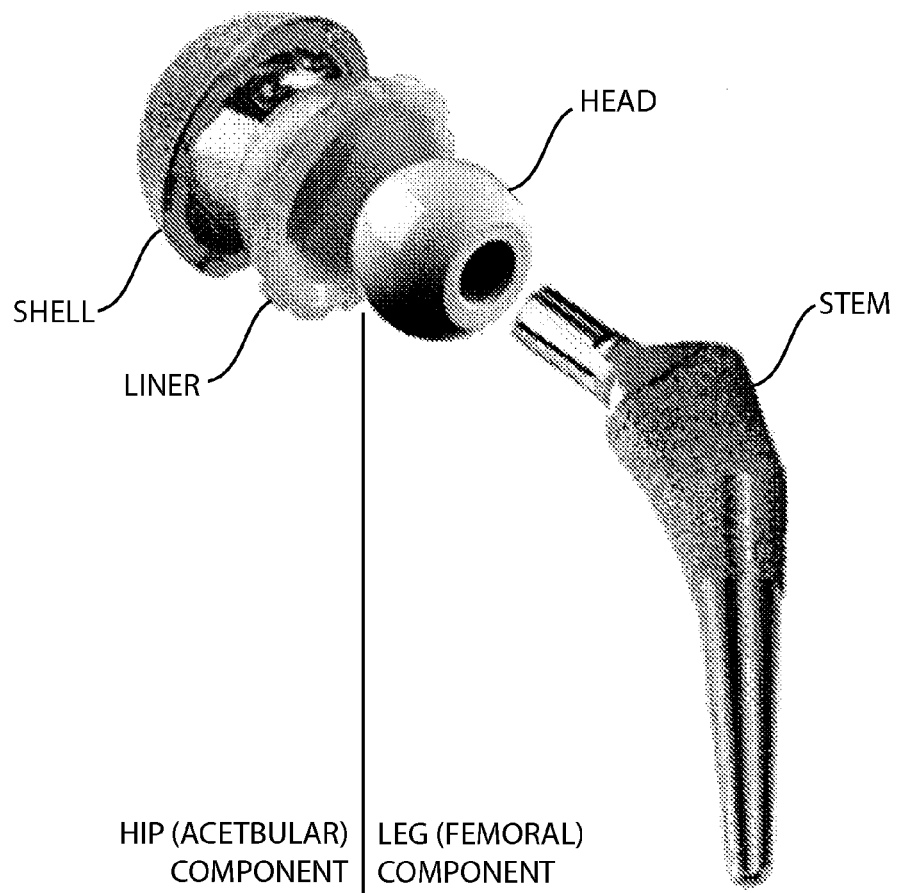
FIG. 1 depicts components of a hip prosthesis, shown in exploded view.
Figure 2A:
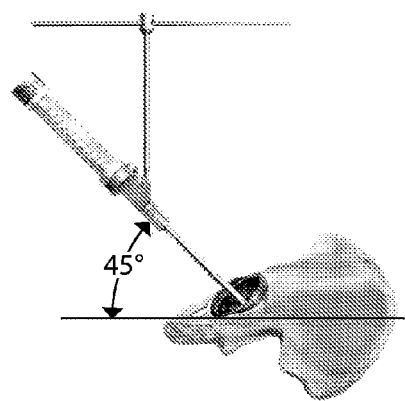
FIG. 2A depicts a cup impactor with attached one kind of visual alignment guide.
Figure 2B:
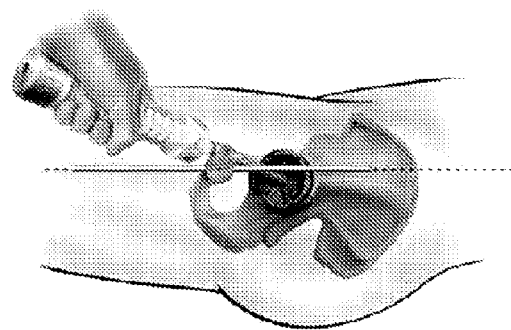
FIG. 2B depicts an overhead view of the cup impactor and attached visual alignment guide of FIG. 2A.
Figure 2C:
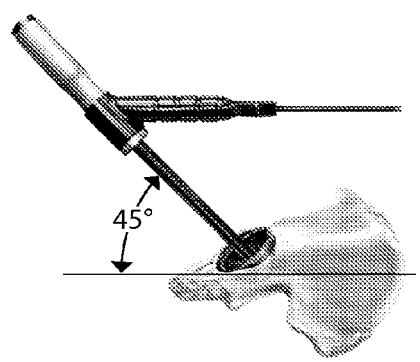
FIG. 2C depicts a cup impactor with attached one kind of visual alignment guide.
Figure 2D:
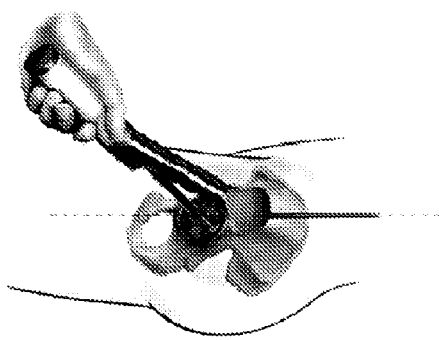
FIG. 2D depicts an overhead view of the cup impactor and attached visual alignment guide of FIG. 2C.

The instant invention includes a novel apparatus, as well as a unique methodology and system, to measure, calculate, and monitor alignment and leg length for precise intra-operative placement and positioning of prostheses, particularly with respect to avoiding acetabular and femoral prosthetic implant malpositioning and leg length discrepancy.

The apparatus of the invention is comprised of multiple digital position, angle, and distance sensors as well as especially designed software. Together the sensors and software electronically measure or calculate:

(1) the bony pelvis' position while lying on the operating table during surgery by using the geometric planes and magnetic field as anatomical reference points. The electronic apparatus is placed and secured in the pelvic axis of the patient and provides accurate and precise measurements of pelvic tilt;

(2) the angles of inclination and forward flexion of the acetabulum before and while being prepared and the acetabular prosthesis while being implanted into the native bone;

(3) the angle of anteversion of the native femur, while the femur is being prepared for the femoral prosthesis and when the stem is being implanted into the native femur; and (4) leg length before and during implantation of the prosthesis.

These measurements are made electronically and, if desired, continuously. They are calculated in real time and in true relationship to the living host's pelvis and body axis during preparation of the host's bone and while the prosthesis is being surgically implanted into the host's native bone structure.

The unique methodology and system is an intra-operative surgical positioning assessment and angle determination made by anatomic alignment. The method and system determine the patient's true pelvic position/tilt by using the geometric planes as anatomical reference planes, i.e., alignment and angles are measured relative to the true horizontal plane, not just to, for example, the operating table. The method and system provide precise information about the angles of inclination and forward flexion of the native bony acetabulum and prosthesis for proper implantation. These measurements and calculations are made in true relationship to the host's pelvis and body axis during the time when the surgeon is preparing the host bone and handling the prosthesis and is inserting it into the host's native bone structure.

A second feature of this apparatus determines anteversion of the native femoral neck while it is being prepared for the prosthesis and when the femoral prosthesis is implanted within the femoral shaft. This provides valuable information for deciding on proper forward flexion of the acetabular prosthesis for each individual patient based on the anatomy.

A third feature monitors any changes in length of the operative leg and assists the surgeon in correcting any pre-existing leg length inequality and avoiding any post-operative leg length discrepancy, which is a common issue.

The measuring sensor units of the present invention utilize inexpensive, highly accurate, digital components able to communicate with a special software program running on a computer processor, personal computer (PC), or hand-held electronic device (e.g., smartphone or electronic tablet), to accurately determine the pelvic tilt, both the angles of inclination and forward flexion of the native acetabulum and prosthesis, anteversion of the native femur and femoral prosthesis, as well as any change in length of the operative limb. The determination of these angles can also be seen and read by the surgeon via a portable digital visual display, thereby removing the need for a PC. In one embodiment, the measuring system continuously monitors the patient's pelvic position and leg length, and as a consequence of this capability, the surgeon can effectively ensure an accurate angular placement of the acetabular prosthesis within the host's native bone and restore the appropriate leg length without compromising stability of the reconstructed joint. The result will be optimum functionality of the joint and patient's satisfaction following surgery, a successful operation.

This measuring system is fast and easy to use; is accurate and precise in its determinations; and is very cost-efficient to operate. The system requires neither sophisticated equipment nor elaborate machinery; and is also able to directly display the prosthesis' placement and any change in leg length, thereby eliminating any subsequent need for repositioning the cup and spending time on inaccurate leg length assessment techniques. In short, the present invention can considerably shorten the time required to complete the entire prosthetic implantation surgical procedure.

I. Words, Terms, and Titles

Although many of the words, terms, and titles employed herein are commonly employed and conventionally understood in their traditional medical usage and surgical context, a summary of detailed descriptive information and definition is presented below for some human anatomic sites, for specific medical phrases and surgical applications, and for particular jargon, designations, epithets or appellations. These points of information, descriptions, and definitions are provided herein to avoid the misinformation, misunderstandings, and ambiguities which often exist; as an aid and guide to recognizing the particulars of the present invention; and for appreciating the true scope and breadth of the present invention.

Figure 3:
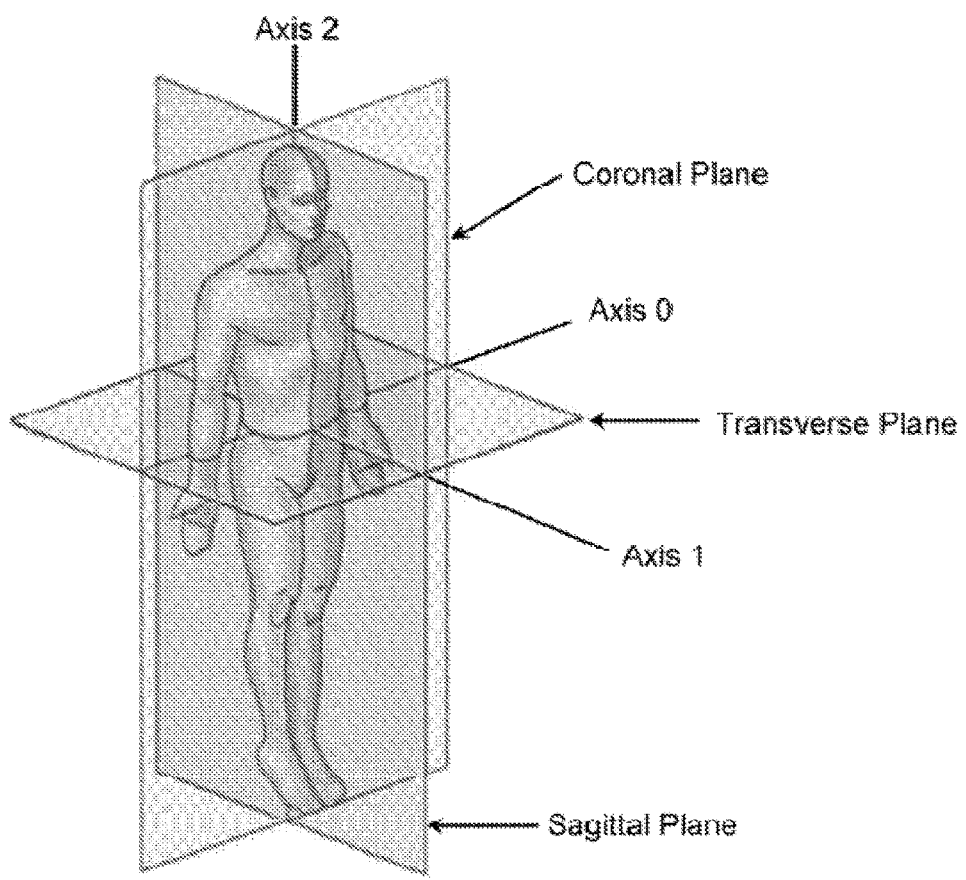
FIG. 3 depicts various anatomic planes and axes of the human body.

Anatomic Planes of the Human Body:

The transverse plane divides the human body into top and bottom sections; the coronal plane divides the body into front (anterior) and back (posterior) portions; and the sagittal plane divides the body into left-sided and right-sided portions. Each of these anatomic planes is illustrated by FIG. 3.

Also by definition and anatomic convention, "Axis 0" is the common line between the transverse and coronal planes; "Axis 1" is the common line between the transverse and sagittal planes; and "Axis 2" is the common line between the coronal and sagittal planes. The pelvic axis is any line defined by the pelvis and generally parallel to Axis 0 or generally perpendicular to the sagittal plane. Each of these anatomic axes is also shown in FIG. 3.

Patient Orientation Information:

A human patient having hip joint replacement surgery is traditionally placed in the lateral decubitus position, i.e., lying down on the side opposite the surgical side. In this position, the patient's operative hip is up.

Alternatively, the patient having hip joint replacement surgery is placed in the supine position, i.e., lying on the back.

The following definitions apply to the lateral decubitus position.

In an ideal situation the "pelvic axis" or "Axis 0" is perpendicular to the horizontal plane and lies parallel to the axis of gravity. Also in an ideal situation, each of Axis 1 and Axis 2 lies parallel to the horizontal plane.

The "axial tilt" is the deviation of Axis 2 (the body's long axis) from the true horizontal plane. Axial tilt is deemed to be zero (0) when Axis 2 is parallel to the true horizontal plane. The axial tilt is assigned a positive value when the patient's head is tilted in a direction below, or his legs are tilted in a direction above, the true horizontal plane. Conversely, the axial tilt is a assigned a negative value in the opposite situation, i.e., when the patient's head is tilted in a direction above, or his legs are tilted in a direction below, the true horizontal plane (see FIG. 4A).

The "anterior-posterior" (or "AP") tilt is the deviation of Axis 1 from the true horizontal plane. AP tilt is zero (0) when Axis 1 is parallel to the true horizontal plane. A forward AP tilt (rotation toward prone position) is assigned a positive value, and a backward AP tilt (rotation toward supine position) is assigned a negative value (see FIG. 4B).

The following definitions apply to the supine position.

In an ideal situation, the pelvic axis or Axis 0 is parallel to the horizontal plane and lies perpendicular to the axis of gravity. Also in an ideal situation, Axis 2 is parallel to the horizontal plane, as in the lateral decubitus position.

The axial tilt is the deviation of Axis 2 from the true horizontal plane. Axial tilt is deemed to be zero (0) when Axis 2 is parallel to the true horizontal plane. The axial tilt is assigned a positive value when the patient's head is tilted in a direction below, or his legs are tilted in a direction above, the true horizontal plane. Conversely, the axial tilt is a assigned a negative value in the opposite situation, i.e., when the patient's head is tilted in a direction above, or his legs are tilted in a direction below, the true horizontal plane (see FIG. 4C).

The "lateral tilt" is the deviation of Axis 0 from the true horizontal plane. Lateral tilt is zero (0) when Axis 0 is parallel to the true horizontal plane. Tilt toward the side of surgery is assigned a positive value, and tilt toward the opposite (non-surgical) side is assigned a negative value (see FIG. 4D).

Other Term Definitions:

The following term definitions are also employed routinely and consistently herein.

Angle of inclination is the angle between the axis of the acetabulum or acetabular implant and the sagittal plane, as projected onto the coronal plane (see FIG. 5A).

Angle of forward flexion is the angle between the axis of the acetabulum or acetabular implant and the coronal plane, as projected onto the sagittal plane (see FIG. 5B).

Angle of anteversion is the angle between the axis of the acetabulum or acetabular implant and the coronal plane, as projected onto the transverse plane (see FIG. 5C).

Figure 6:
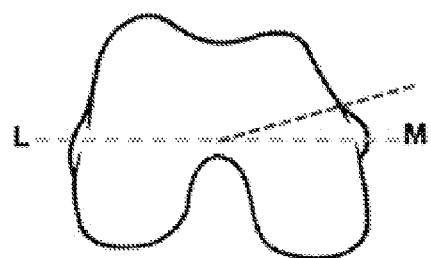
FIG. 6 depicts a transverse section through a distal femur at the level of the lateral (L) and medial (M) condyles. The dashed line between L and M is the epicondylar axis. The acute angle defined by the two dashed lines is the angle of angle of anteversion of the femur. In this view anterior is up and posterior is down.

Angle of anteversion in femur is the angle between the axis of the femoral neck and the epicondylar axis (of the distal femur). See FIG. 6.

Epicondylar axis is a line connecting medial and lateral epicondyles of the distal femur. See FIG. 6.

Angles are "absolute" angles when measured relative to the actual horizontal level.

Angles are "true" angles if and when measured relative to the actual position of the patient's pelvic axis and sagittal or coronal planes, respectively.

Figure 5:
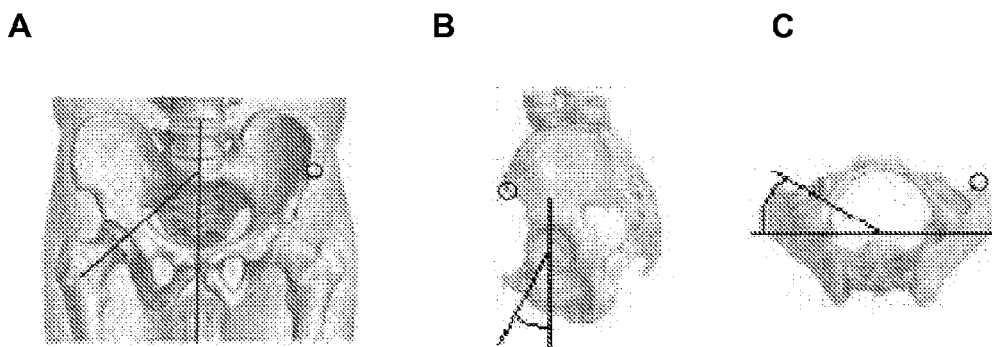
FIG. 5 depicts the angles of inclination (A), forward flexion (B), and anteversion (C). Circles in the different views show one anterior superior iliac spine (ASIS).

Anterior superior iliac spine (or "ASIS") is the most prominent anterior bony landmark of each side (wing) of the pelvis (see FIG. 5). Thus, normally there is a left ASIS and a right ASIS.

The methodology and system of the present invention will reveal:

(1) patient's pelvic axis position in space over the time the surgical operation is being performed. These positional measurements are used in turn as a major reference point to determine the appropriate inclination angle, as well as the forward flexion of the acetabular implant, so that any pelvic tilt may be quickly detected and the prosthesis may be implanted in the best possible biomechanical position;

(2) degree of the anteversion of the femoral neck. It is considered with forward flexion of the cup as combined anteversion of the reconstructed joint; and (3) any change in length of the operative leg that is a common undesired outcome in hip arthroplasty.

II. Components of the System of the Invention

There are six components comprising the measuring and alignment device: an axis guide (AG); a first electronic sensor (ES1); a second electronic sensor (ES2); an electronic angle sensor (AS); an electronic distance sensor (DS); and operative application software. In certain embodiments, ES1 or ES2 may be absent. Each component is described individually below.

1. Axis Guide

The axis guide (AG) is a rigid bar that serves as a structure for determining position and angles for attaching electronic sensor ES1 to the native bony pelvis of the patient.

Figure 7A:
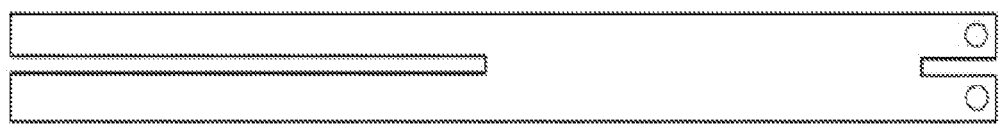
FIG. 7A depicts an overhead view of an axis guide.

In one embodiment, the axis guide is a rigid bar having fixed length, width and depth dimensions, said bar being formed of resilient material which is constructed and arranged so that it can be positioned in, or placed to lie parallel to, the patient's pelvic axis by the surgeon. One embodiment of an axis guide is illustrated by FIG. 7A. The axis guide can, but need not necessarily, be made of material that can be sterilized. Moreover, the axis guide can, but need not necessarily, be sterilized for use in accordance with the method of the invention.

In the overhead view shown in FIG. 7A, there is a slot at each end of the axis guide which is used for visualizing and properly placing the axis guide upon marked anatomic spots made by the surgeon on the skin of the patient (as described in detail hereinafter). The slot can be of lesser length on the surgical end (the end closest to the surgical side) and of greater length on the opposite end, and thus will accommodate different sizes of pelvis.

The axis guide also has two threaded apertures lying adjacent to the slot at the surgical end, to receive two threaded pin guides for the subsequent insertion therethrough of securing pins. The pin guides are to be placed perpendicular to pelvic axis, and they identify the proper place for attaching the ES1 unit sensor (see below).

The pin guides are cylinder-shaped articles made of material compatible for use with the axis guide. In one embodiment, the pin guides are made of the same material as the axis guide. The pin guides are, on their outer aspect, threaded at one end such that they can be receivably introduced into the threaded apertures of the axis guide at 90° angles. The inner diameter of each pin guide is just large enough to allow passage of a securing pin so as to permit free rotation of the securing pin with essentially no friction and no play.

Figure 7B:
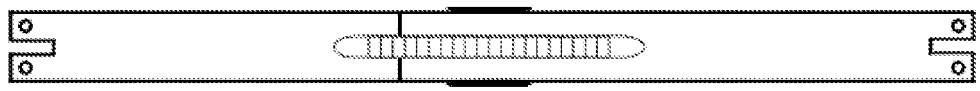
FIG. 7B depicts an overhead view of an alternative embodiment of an axis guide.

In one embodiment, the axis guide comprises two rigid bars slidably connected to each other so as to create a single unit with adjustable length. The bars have fixed width and depth dimensions and are comprised of resilient material such as stainless steel. The adjustable length axis guide is constructed and arranged so that it can be positioned in, or placed to lie parallel to, the patient's pelvic axis by the surgeon. A slot at each end of the axis guide is used for visualizing and properly placing the axis guide upon marked anatomic spots made by the surgeon on the skin of the patient (as described in detail hereinafter). The adjustable length of the axis guide is designed to accommodate different sizes of pelvis. An overhead view of this embodiment of an axis guide is illustrated by FIG. 7B.

There is a releasable locking mechanism in the mid section of the adjustable length axis guide. Length of the axis bar can be adjusted when the locking mechanism is released. Once engaged, the locking mechanism keeps the length constant.

This embodiment of the axis guide also has two threaded apertures lying adjacent to the slot at each end, to receive two threaded pin guides for the subsequent insertion therethrough of securing pins. The pin guides are to be placed perpendicular to the pelvic axis, and they identify the proper place for attaching the ES1 unit sensor (see below).

In one embodiment, a physical measuring apparatus is integral to the mid section and indicates the distance between pin guides on each end. For example, as shown in FIG. 7B, the measuring apparatus is a ruler fixed or integral to one of the bars; the distance is read off the ruler at a point indicated on, or set by the end of, the other bar. In one embodiment, the ruler is calibrated in millimeters. This distance read off the measuring apparatus is equal to the distance between right and left ASIS in the patient.

Figure 8:
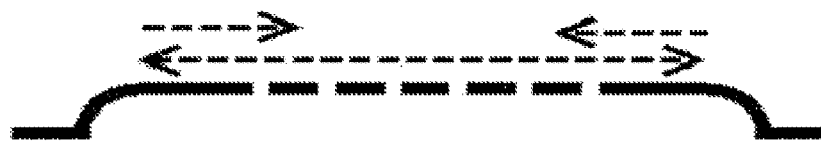
FIG. 8 depicts a side view of an alternative embodiment of an axis guide.

An alternative embodiment of the axis guide may be employed if needed to accommodate patients having a large abdomen. An example of such alternative axis guide is shown in FIG. 8 as a generally "Ω"-shaped construct having an adjustable-length central straight portion; two curved sections adjustably attached to the central straight portion; and two straight ends, each of which is connected to one curved section. The two straight ends occupy substantially the same plane and are substantially parallel to the central portion. At the surgical end there is a short length slot and two adjacent threaded holes for receiving the pin guides, and on the opposite end there is also a short length slot. In one embodiment, the two straight ends are identical, i.e., each straight end has a short length slot and two adjacent threaded holes suitable for receiving the pin guides. A key difference between the embodiments of FIGS. 7 (A and B) and FIG. 8 is the central portion, which creates more space between two straight ends to fit on patients with large abdomens.

2. First Electronic Sensor (ES1)

Figure 11:
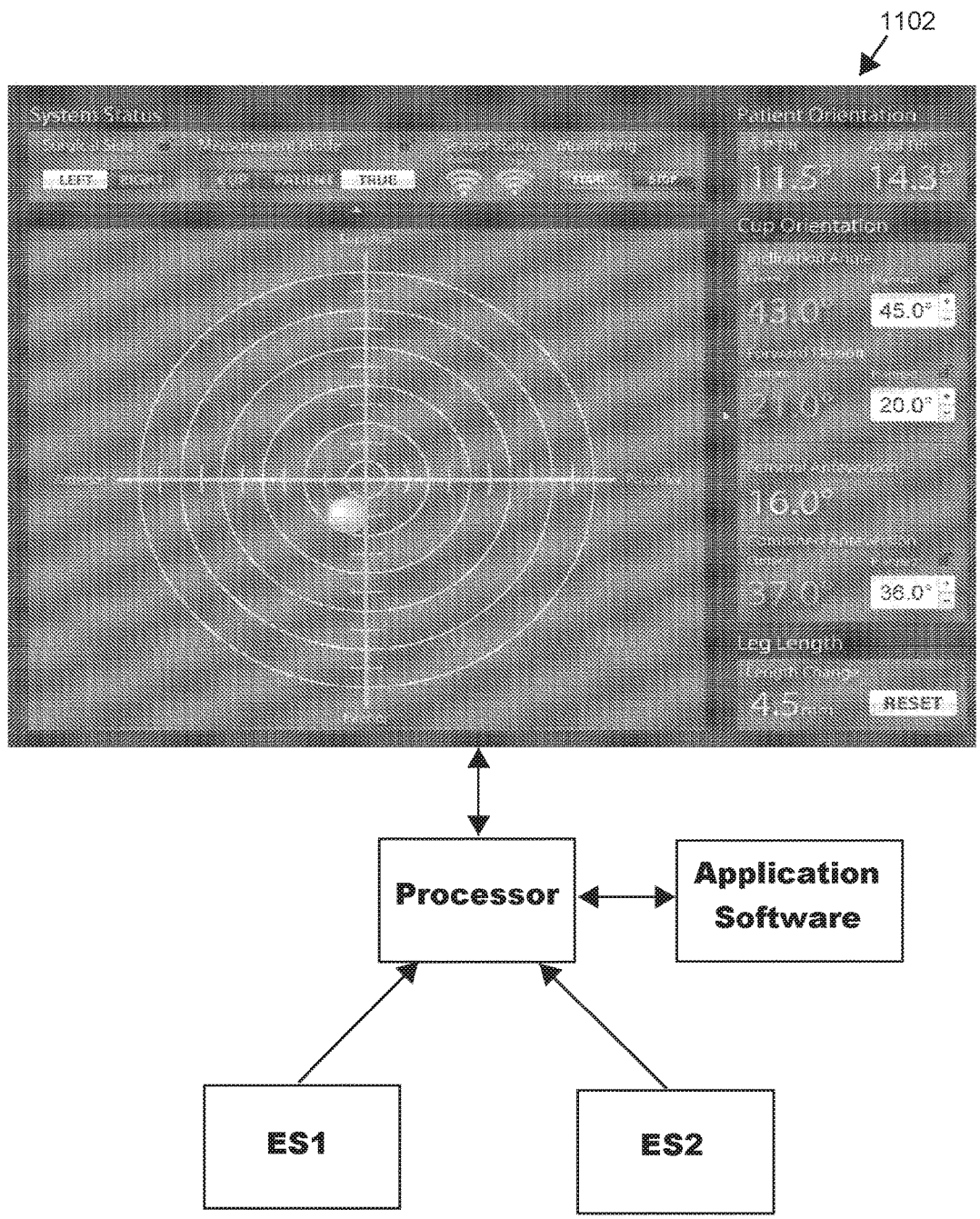
FIG. 11 depicts a representative screen shot of application software, indicating patient orientation; planned and current values of inclination angle, forward flexion, femoral anteversion, and combined anteversion; leg length change; and a graphical representation of positioning.

Electronic sensor #1 (or "ES1 unit") is a micro-electromechanical system (MEMS) multi-axis position sensor that is calibrated in all three Axes 0-2. Measuring the position in Axis 1 and Axis 2 reveals the pelvic axis and AP tilt, respectively. Measuring position in Axis 0 is required as the reference axis for calculating the cup's forward flexion angle. This unit is designed to be attached to bony pelvis at an ASIS, e.g., by securing pins as described herein. In one embodiment, the ES1 unit wirelessly communicates with a computer processor, PC, or hand-held electronic device running the application software, as shown in FIG. 11.

3. Second Electronic Sensor (ES2)

Electronic sensor #2 (or "ES2 unit") is an electronic position and rotation sensor much like the ES1 unit, and it also is calibrated to make digital measurements in all three Axes 0-2, respectively. The ES2 unit measures the absolute angles for determining the position of the acetabular prosthetic implant as a single electronic calculation. The true angles of inclination and forward flexion are calculated by the application software when the ES2 unit is used in combination with the ES1 unit. In one embodiment, the ES2 unit communicates wirelessly with the computer processor, PC, or hand-held electronic device running the application software, as shown in FIG. 11. In one embodiment, the ES2 unit communicates wirelessly with the ES1 unit.

As described below via the exemplary hip joint prosthetic surgery, the ES2 unit is primarily focused upon determining the position of the acetabular prosthesis when the latter is being implanted in situ. To achieve this purpose, the ES2 unit is typically secured to the cup impactor in order to show the true position and placement orientation for the implanted prosthesis at that moment in time.

Accordingly, the ES2 unit measures the absolute angles for both of two different parameters: (i) the absolute angles then existing for the host's acetabulum (i.e., the patient's hip socket); and (ii) the absolute angles of the acetabular prosthesis then being implanted by the surgeon.

4. Angle Sensor (AS)

Figure 9:
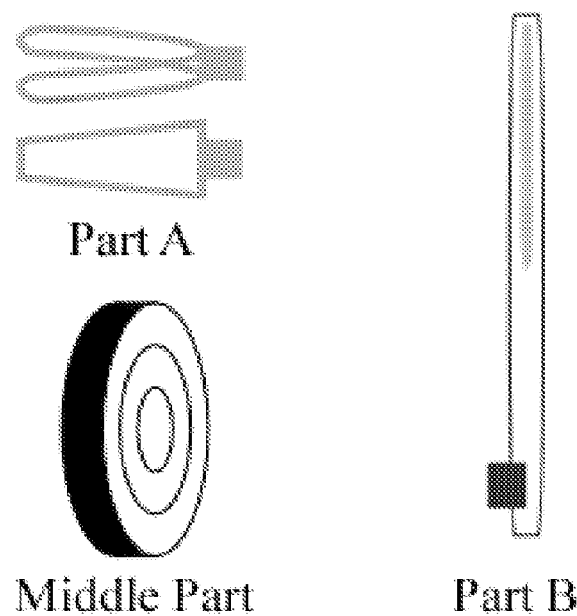
FIG. 9 depicts components of an electronic angle sensor (AS). Part A and Part B correspond to arms that can be rotatably connected to a common pivot point of Middle Part, which comprises an electronic angle sensor device.

An electronic angle sensor (or "AS" unit), in one embodiment, comprises three parts: Part A, designed to be either inserted into the native femoral neck, attached to a broach handle, or placed on the implanted femoral stem; Part B, comprising a light pointer, e.g., light-emitting diode (LED) (like a laser pointer used in presentations); and a middle part, Part C, comprising an electronic angle sensor device, to which Parts A and B are attached. One end of each of Parts A and B is constructed and arranged to attach to Part C. So attached, Part A and Part B are free to rotate, like hands on a clock (see FIG. 9). The electronic angle sensor device integrated in Part C reads the angle between Part A and Part B. When in use, Part A is inserted into the femoral neck (after making the neck cut) or placed on the implanted stem, then Part B is rotated until the light pointer is shined in the midline on back of the operative lower leg. At this position, Part B is parallel to the long axis of the lower leg and is perpendicular to the epicondylar axis of the distal femur. The angle between Part A and Part B, minus 90 degrees, is equal to anteversion of the native neck or implanted stem, measured by the integrated electronic sensor and read by the application software. The measurement will be eventually considered in calculating the combined anteversion of the reconstructed joint (i.e., the sum of the angle of forward flexion of the cup and the angle of anteversion of the stem).

In one embodiment, Part A has an integrated electronic position sensor, similar to ES1 or ES2. In one embodiment, Part B has an integrated electronic position sensor, similar to ES1 or ES2.

5. Distance Sensor (DS)

The distance sensor is a leg length measurement unit comprised of three parts: (1) a substantially planar solid component, comprising two holes designed to be attached to the securing pins installed in the ASIS (constant portion of the leg length), creating a fixed reference position; (2) an electronic distance sensor (DS) unit attached to the first, substantially planar component, capable of measuring the distance from a reflection pin (RP); and (3) a reflection pin (RP) constructed and arranged to be placed in (attached to) the femur (the variable part of the leg length). In one embodiment, the first, planar component is a Y-shaped or diapason (tuning fork)-shaped bracket (DB) that is bent or angled at each fork end, wherein each of the two fork ends comprises a hole to accept the exposed end of one securing pin. The DS sensor of the unit communicates with the application software to reveal any change in length of the operative leg during the operation.

In an alternative embodiment, the distance sensor is a leg length measurement unit comprised of three parts: (1) a substantially planar solid component, comprising two holes designed to be attached to the securing pins installed in the ASIS (constant portion of the leg length), creating a fixed reference position; (2) a third electronic position sensor (ES3), much like the ES1 unit, attached to the first, substantially planar component; and (3) a fourth electronic position sensor (ES4), much like the ES1 unit, constructed and arranged to be placed in (attached to) the femur (the variable part of the leg length). Position information provided by ES3 and ES4 can be used to determine the distance between ES3 and ES4. In one embodiment, the first, planar component is a Y-shaped or diapason (tuning fork)-shaped bracket (DB) that is bent or angled at each fork end, wherein each of the two fork ends comprises a hole to accept the exposed end of one securing pin. ES3 and ES4 communicate with the application software to reveal any change in length of the operative leg during the operation.

6. Application Software

The application software is an especially designed and coded program which is operative to read the information sent from the ES1, ES2, AS, and DS sensors; display the axial or AP tilt angles, and/or the absolute inclination and forward flexion angle values; calculate the true angles of inclination and forward flexion; display the femoral anteversion; and monitor any changes in leg length.

The functions and processes recited above may be implemented in software, hardware, firmware, or any combination thereof. The processes are preferably implemented in one or more computer programs executing on a programmable computer including at least one processor, a storage medium readable by the processor (including, e.g., volatile and non-volatile memory and/or storage elements), user input devices (e.g., the sensors described above, a keyboard, a computer mouse, a joystick, a touchpad, a touchscreen, or a stylus), and one or more output devices (e.g., a computer display). Each computer program can be a set of instructions (program code) in a code module resident in the random access memory of the computer. Until required by the computer, the set of instructions may be stored in another computer memory (e.g., in a hard disk drive, or in a removable memory such as an optical disk, external hard drive, memory card, or flash drive) or stored on another computer system and downloaded via the Internet or other network.

The foregoing components, and in particular the application software, is used in conjunction with a computer processor, PC, or hand-held electronic device capable of running the application software. Computers of varying kinds, capacities, and features are commercially available today and commonly employed. The particular choice of computer is thus solely a personal and individual choice, as long as it is capable of running the application software.

The computer processor, PC, or hand-held device will include or be connected to an electronic visual display, which will display the communicated and calculated measurements. For example, the visual display could be either the computer's monitor or a display portion of the hand-held device. FIG. 11 illustrates one embodiment of a computer processor running application software that communicates with electronic sensors and displays communicated and calculated measurements.

Any or all electronic communication connections typically will be provided either as a wireless mode of communication or a hard-wire manner of communication employing a Universal Serial Bus (USB) and a standard USB cable, or by any combination of wireless and hard-wired connections. For example, in one embodiment, all the electronic sensors are wirelessly connected to the computer processor, PC, or hand-held electronic device running the application software, while the electronic visual display is hard-wire connected to the computer processor, PC, or hand-held electronic device running the application software.

III. Methods of the Present Invention

For ease of understanding and gaining a better appreciation of the subject matter as a whole comprising the present invention, a representative example describing a complete hip joint replacement is presented in detail below. It will be expressly understood, however, that the particular preferences and optimal details of this specific example are neither restrictive nor limiting of the method and system as a whole, and that many variations of the exemplary method and system are envisioned which may be advantageously and beneficially employed.

The methodology and system of the present invention will reveal the patient's true pelvic axial orientation during the time the surgical implantation operation is being performed. These axial orientation measurements in turn are used as major reference points then to determine the appropriate angle of inclination angle, as well as the angle of forward flexion of the acetabular implant, such that any existing pelvic tilt may be quickly detected, and that the implanted prosthesis may be properly positioned and oriented into the pelvis in the best possible biomechanical position.

The methodology for precise intra-operative placement and positioning of a prosthesis as a surgical implant into the native pelvic bone structure of a living subject is performed in accordance with the following four manipulative steps:

Step 1: Accurately reproducing the patient's pelvic axis.

The patient's pelvic axis is properly and accurately reproduced by connecting two identical spots on the pelvis, each on either side of the sagittal plane or midline. The ASIS is the most prominent bony landmark on the anterior aspect of the pelvis, readily identified with gentle palpation on all patients, regardless of their size, sex, or age.

When the patient is placed in a supine position, each ASIS is located by palpation and then visibly marked on the skin surface on each side of the pelvis. The pelvic axis is a straight line connecting the right and left ASIS.

In one embodiment, the host's pelvic axis is then physically drawn upon and over the skin surface as a readily visible straight line connecting the right and left ASIS.

Note that the pelvic axis must be perpendicular to the midline. A helpful accessory device by which to perform this step accurately and quickly is a laser cross-pointer that is designed or suitable for this particular purpose. In addition, the pre-operative pelvis x-rays should be reviewed in advance by the surgeon for any possible anatomic asymmetry and pelvic obliquity.

A variety of different approaches are available for securing the ES1 unit.

The axis guide of choice is physically placed on the marked spots or pelvic axis line in conformity with and in order to reproduce the host's pelvis axis. The slot on either end of the axis guide is centered over the marked right and left ASIS.

In one embodiment, particularly suitable for a "posterior approach" surgical procedure, the end of the axis guide that has the threaded apertures for receiving pin guides is placed on the side of operation (operative side). The threaded apertures of the axis guide are positioned in or parallel to the sagittal plane transecting the marked operative-side ASIS. This step of positioning the axis guide can be performed either prior to or after starting anesthesia.

In one embodiment, particularly suitable for an "anterior approach" surgical procedure, the end of the axis guide that has the threaded apertures for receiving pin guides is placed on the side opposite operation (non-operative side). The threaded apertures of the axis guide are positioned in or parallel to the sagittal plane transecting the marked non-operative-side ASIS. This step of positioning the axis guide can be performed either prior to or after starting anesthesia.

After starting anesthesia while the patient is still in supine position, and using sterile technique, two sterile pin guides are attached to one end of the axis guide positioned on the pelvic axis. Once in place, these pin guides are perpendicular to the long axis of the axis guide and, thus, perpendicular to the pelvic axis.

A securing pin is passed through each pin guide and firmly pushed against the skin. Each pin's sharp tip incises and traverses the skin to contact the bone of the ASIS. Then the securing pins are advanced into the bone using either a hand driver tool or power driver tool attached to their exposed ends.

By this technique, the securing pins will be placed parallel to Axis 1 and lie perpendicular to Axis 0 and Axis 2. The securing pins are preferably about 3 mm in diameter, but such securing pins come in different lengths (and diameters) to accommodate different body sizes with different amounts of soft tissue overlying the ASIS.

Securing pins are thus placed in ASIS of the operative side in "posterior approach" and in ASIS of the non-operative side in "anterior approach".

When properly performed, the accuracy of this technique for correctly reproducing the pelvic axis is essentially 100 percent.

Following placement of the securing pins, the axis guide, together with associated pin guides, is removed by sliding the axis guide assembly off (over) the exposed ends of the securing pins.

In one embodiment, after removal of the axis guide and associated pin guides, a sterile 4"×4" adhesive foam tape with two suitably spaced and sized, e.g., 3.0 mm, holes is then attached to the skin by passing the exposed ends of the securing pins through the holes. This adhesive foam tape prevents any possible stretch and damage by holding the skin around the punch holes made by passing the securing pins through the skin.

In a first alternative embodiment, the axis guide is positioned on the pelvic axis and secured in place using foam tape. The adhesive foam tape wraps around the entire body at the same level, functioning as a belt. The ES1 unit is attached to axis guide.

In a second alternative embodiment, a stretchable girdle is fitted onto the patient and used for securing the axis guide. If and when so used, the stretchable girdle typically is a one-legged garment which will extend from the patient's waistline, above the ASIS, to the thigh on the opposite (non-operative) side of the body. A proximal belt is used to keep the girdle from slipping longitudinally, and a transverse belt will also further hold the girdle and prevent lateral movement. The bar of the axis guide is then placed in the transverse front sleeve of the girdle and then the ES1 unit sensor is attached.

After rotating the patient to the lateral decubitus body position, the final location for the secured axis guide is again confirmed as being correct. The patient can then be prepped and draped in usual fashion for surgery.

Step 2: Attaching the DS Unit

In one embodiment, a diapason-shaped bracket is attached, at the bent fork ends, to the two securing pins, already inserted into ASIS, by passing exposed ends of the securing pins into or through suitably sized and positioned holes in the bent fork ends. A distance sensor (DS) is attached to the handle end of the diapason-shaped bracket. After surgical exposure of the hip joint and before dislocating the femur to make the neck cut, a reflecting pin is inserted into the greater trochanter of the operative femur, thereby providing a reference point (RP).

In one embodiment, the distance between DS and RP right after placing the reflecting pin into the greater trochanter is measured in a neutral position as a reference pre-operative leg length. Any change in leg length will be sensed by the DS and reported by the system of the invention.

Step 3: Placing the Sensor Units

The ES1 unit, which is provided in a sterile package, is attached by its base to the exposed ends of the securing pins. In one embodiment, a protective cap or cover is placed over the installed ES1 to reduce any risk of accidental damage to ES1 during the operation.

The DS unit is attached to its bracket. In one embodiment, the DS unit is attached to the handle end of a diapason-shaped bracket. After surgical exposure of the hip joint and before dislocating the femur to make the neck cut, a reflecting pin is attached to the greater trochanter of the operative femur, thereby providing a reference point.

The ES2 unit, which is provided in a sterile package, is then attached to a cup impactor by a universal connector (a clip-like connector that can connect to any broach handle regardless of its shape. The cup impactor is fitted with either a trial cup to evaluate forward flexion of the native acetabulum or the actual cup prosthesis and placed into position in preparation for implantation of the cup.

Figure 10:
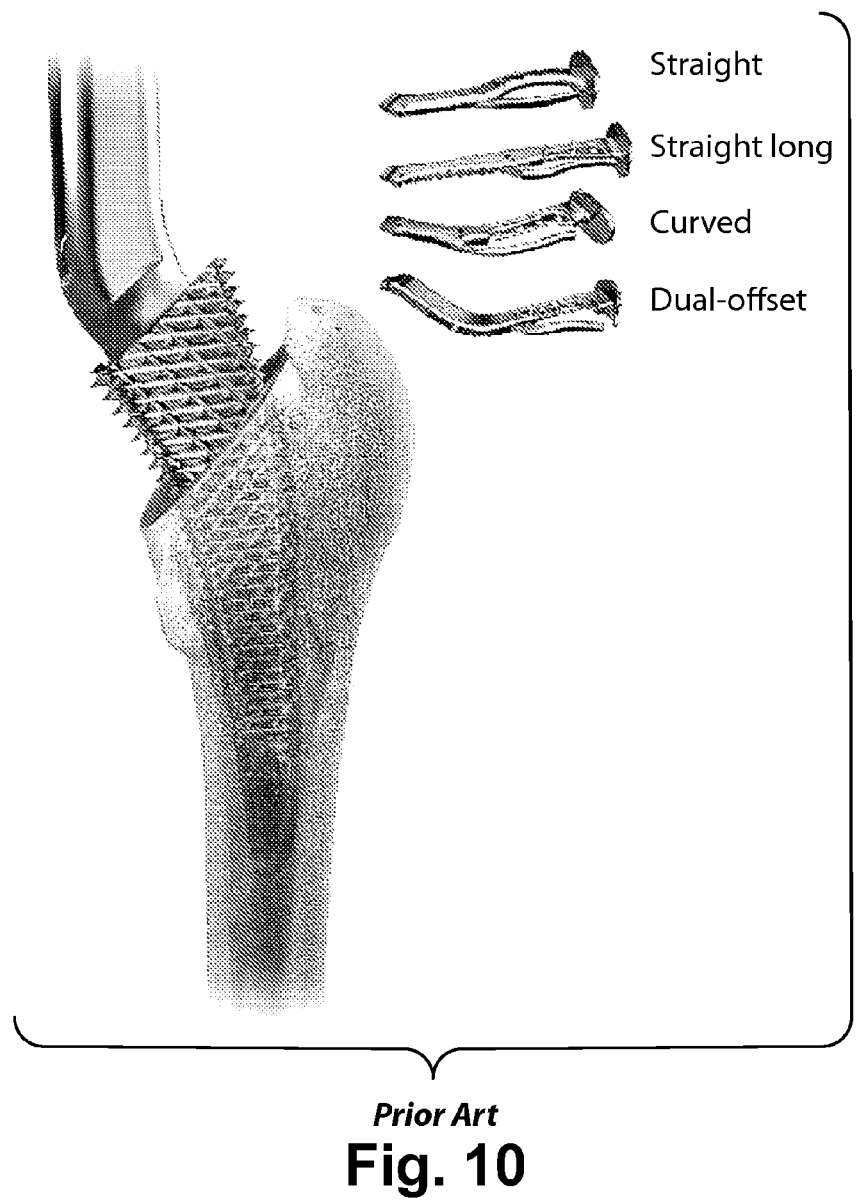
FIG. 10 depicts a broach fitted with a handle and various embodiments of broach handles.

The AS, which is provided in a sterile package, is releasably attached to one or more broach handles or the prosthesis by Part A. See FIG. 9. A broach handle is a handle attached to a broach, the latter being a tapered chisel tool used to prepare the femoral canal to receive the stem of the prosthesis. Broach handles themselves are typically releasably attached to a broach. See FIG. 10. Typically two broach handles are alternatingly used during each operation. In one embodiment, the AS has a quick-release locking mechanism for attaching to a broach handle and can be attached to any of a variety of broach handles.

Step 4: Position Assessment and Monitoring

The application software is used to calculate and visually display the position angles. A sample screenshot 1102 of the application software is shown in FIG. 11, where the surgeon enters the desired position angles in the corresponding boxes. When monitoring patient and prosthesis position angles, the software provides real-time numeric and visual feedback assisting surgeon in placing the implant in proper direction and alignment.

The methodology preferably offers the surgeon not less than three different mode of use options, each of which can be individually selected, for example, by turning a mode selector knob, after selecting a particular surgical approach.

Mode #1: True Angles

The patient is placed into surgical position and each planned or desired angle is entered into the application software in the corresponding window, field, or box. The application software then calculates and presents the true angles of inclination and forward flexion based on information provided by both the ES1 unit and the ES2 unit.

Neutral positioning of the pelvis is not an issue since true angles are calculated by the application software. Deviation less than 5° from the planned angle is considered acceptable and may be shown, for example, with a green background. Any deviation between 5-10° or greater than 10° triggers a warning with, for example, yellow and red background, respectively.

In addition, since the respective angles are calculated in relation to the pelvis true position rather than in relation to moveable objects, regardless of primary deviation or any change in patient's position that may occur during the operation, the surgeon is nevertheless certain that the implant is being placed in the planned and correct position. The accuracy of the sensors is typically set at ±0.1°.

Mode #2: Pelvis Position Only

With only the ES1 unit connected to the remotely located computer processor, PC, or hand-held electronic device, the visual display device displays only the axial and AP tilt information. Given this information, the patient's position can then be either adjusted or considered when placing the cup. The displayed information is most useful in constantly showing any change in the patient's position that may occur after draping or during the actual implantation operation, and the surgeon can make any appropriate adjustments and fine-tune the positioning of the prosthesis while the patient is still on the operating table. Typically, the cup's angles will show 0.00 values or otherwise indicate that the ES2 is not being used.

Mode #3: Cup Position Only

With only the ES2 unit connected to the remotely located computer processor, PC, or hand-held electronic device, the system measures the absolute angles of inclination and forward flexion relative to the horizontal level and presumed Axis 2. In utilizing this mode, the surgeon assumes that the patient has been placed at neutral angles and thus any meaningful deviation from the neutral angles will become immediately apparent. Monitoring the patient's position, however, is not possible in this mode.

Leg length can be measured and displayed by the application software in each of the three modes just described.

IV. Major Advantages and Benefits of the Invention

The present invention provides the surgeon with many major advantages and desirable benefits. Among them are the following:

Reliability.

The reference plane for body/pelvis tilt is the horizontal plane, which is in turn based on the axis of gravity. The axis of gravity is a constant parameter on all different surfaces, from horizontal to steep, and all around the world. The electronic components are sensitive and capable to measure any deviation from horizontal position in both Axis 1 and Axis 2.

All the conventionally known and used methods (except computerized navigation) are based on the assumption that the patient is lying down parallel to the operating table and the table itself is parallel to the floor of the operating room. In contrast, the present invention does not rely on such assumption and can function accurately even if the operating table is not horizontally leveled. It is not uncommon that for different medical reasons the operating table has to be tilted to some extent.

Precision.

The desired angles are measured electronically with very high accuracy and sensitivity (<0.01°). All other methods (except computerized navigation) are either based on visually estimating the angles or, in the better cases, using physical devices with very low accuracy >10°. That could be the reason that many literature reports consider up to 10° of deviation to be within an acceptable range. The greater degree of accuracy provided by the invention will elevate the standards for and quality of hip arthroplasty.

Ease of Use.

The apparatus of the present invention can be set up and used by any member of the surgical team. This is in marked contrast to computerized navigation systems which require a long period of technical training before being used.

Simplicity.

The present invention employs only a few small basic components and can use any conventional computer processor, PC, or hand-held electronic device. This fact makes the apparatus far less vulnerable to malfunction and failures; and allows for very easy replacement of component parts if and when necessary. In comparison, computerized navigation requires one or two large units of cameras and highly sophisticated computers, and it uses many different probes for registration.

Compact Size.

The apparatus of the present invention, apart from the axis guide and the PC, is very small in size and is extremely light in weight. The whole apparatus weighs a fraction of a pound, and the electronic components are typically of matchbox size. In actual practice, the apparatus does not take up any meaningful space in the operating room.

In comparison, the computerized navigation system is very bulky and heavy. It can only be used in a large size operating room. In addition to its large size, since the system has to be kept out the sterile operating field while the cameras aim at the special spheres with no object passing in between them, the true setup requires even more space and limits number of the efficient assistants or people in training Low Cost of Acquisition.

The true cost of the present invention is estimated to be less than 1% of a computerized navigation system.

Time Savings.

By helping the surgeon position and orient the prosthetic implant at the correct angle during the first attempt—with no further need to reevaluate and reposition the placement—the present invention considerably shortens the time needed for completing the operation.

In contrast, computerized navigation systems invariably add at least 30-45 minutes to the surgical operation time in order to register and process the data.

Cost Savings.

By shortening the operative time, the present invention also lowers the expense of the surgical operation and increases the productivity of the surgeons and operating rooms.

In contrast, computerized navigation systems need a pre-op CT scan, which itself is an expensive procedure.

Reduced Morbidity.

By helping to position the prosthetic implant in the correct angle in a single attempt, the present invention increases the durability of the prosthesis and lowers any risk for re-operation in future. In addition, by shortening the operation time, it also lowers the risk of infection.

Effort Savings.

All the present invention requires is the attachment of the apparatus. In contrast, the computerized navigation systems require pre-op planning and transferring the data from CT scan to computer unit, which average about 30 min/case. This additional time requirement is almost one third of the time otherwise needed for a total hip arthroplasty operation. It therefore needs to be considered that in case of any technical problem encountered during an operation, from a power failure to a malfunction of the PC or digital media used to transfer the data from unit to unit, this process needs to be repeated.

Resource Savings.

As mentioned above, all computerized navigation systems require a pre-op CT scan of the patient's pelvis. This results in patients needing to spend more time and money for an extra procedure in radiology, a very busy department in most hospitals. In comparison, the present invention does not require any extra preparation tasks to be performed.

The present invention is not restricted in form nor limited in scope except by the claims appended hereto.

I claim:

1. A method for precise intra-operative positioning of a total hip prosthesis in a human subject, comprising:
   determining a pelvic axis of a human subject in need of hip arthroplasty;
   attaching a first electronic position sensor (ES1) to a bony anatomic site on the pelvic axis of the subject;
   attaching a second electronic position sensor (ES2) to a cup impactor, wherein the first and second electronic position sensors are capable of acting in combination to report information useful to calculate a true angle of inclination and a true angle of forward flexion of an acetabular prosthetic cup;
   contacting the cup impactor with the acetabular prosthetic cup that is to be implanted into a prosthetic implantation site in the subject;
   transferring information from the first and second electronic position sensors to a computer processor running application software, wherein the application software calculates the true angle of inclination and the true angle of forward flexion of the acetabular prosthetic cup; and displaying results of the calculations on an electronic visual display device while the prosthesis is being surgically positioned for implantation into the subject.

2. The method of claim 1, wherein the calculated measurements are displayed on demand.

3. The method of claim 1, wherein the calculated measurements are displayed continuously.

4. The method of claim 1, further comprising attaching an electronic angle sensor to a structure selected from the group selected from native femoral neck, prosthetic femoral stem, and broach handle, wherein the electronic angle sensor is capable of reporting information useful to calculate an angle of anteversion of the structure to which it is attached; and transferring information from the electronic angle sensor to the computer processor running application software, wherein the application software calculates the angle of anteversion of the structure to which it is attached.

5. A method for precise intra-operative positioning of a total hip prosthesis in a human subject, comprising:

determining a pelvic axis of a human subject in need of hip arthroplasty;

attaching a first electronic position sensor (ES1) to a bony anatomic site on the pelvic axis of the subject;

attaching a second electronic position sensor (ES2) to a cup impactor, wherein the first and second electronic position sensors are capable of acting in combination to report information useful to calculate a true angle of inclination and a true angle of forward flexion of an acetabular prosthetic cup;

contacting the cup impactor with the acetabular prosthetic cup that is to be implanted into a prosthetic implantation site in the subject;

attaching an electronic leg length measurement unit, comprising (i) a reflection pin configured to be attached to one of a femur or a pelvis of the human subject; and (ii) an electronic distance sensor (DS) capable of being attached to the other of the femur or the pelvis of the human subject and capable of reporting, to a computer processor, information about its distance from the reflection pin;

transferring information from the first and second electronic position sensors to the computer processor running application software, wherein the application software calculates the true angle of inclination and the true angle of forward flexion of the acetabular prosthetic cup;

transferring information from the electronic distance sensor to the computer processor running the application software, wherein the application software calculates the distance between the distance sensor and the reflecting pin; and displaying results of the calculations on an electronic visual display device while the prosthesis is being surgically positioned for implantation into the subject.

6. The method of claim 5, wherein the calculated measurements are displayed on demand.

7. The method of claim 5, wherein the calculated measurements are displayed continuously.

8. The method of claim 5, wherein the leg length measurement unit further comprises a substantially planar bracket constructed and arranged to receive at least two securing pins spaced and oriented in accordance with apertures of an axis guide; and wherein the electronic distance sensor (DS) is configured to be attached to the bracket.

9. The method of claim 5, further comprising attaching an electronic angle sensor to a structure selected from the group consisting of a native femoral neck, a prosthetic femoral stem, and a broach handle, wherein the electronic angle sensor is capable of reporting information useful to calculate an angle of anteversion of the structure to which it is attached; and transferring information from the electronic angle sensor to the computer processor running application software, wherein the application software calculates the angle of anteversion of the structure to which it is attached.

10. The method of claim 5, wherein the pelvic axis is (i) parallel to a common line between the human subject's transverse and coronal planes, or (ii) perpendicular to the human subject's sagittal plane.

11. The method of claim 5, wherein the electronic visual display device is located remotely from the first electronic position sensor (ES1) and the second electronic position sensor (ES2).

12. The method of claim 5, wherein determining the pelvis axis includes placing an axis guide in contact with an anterior superior iliac spine (ASIS) on a left and a right side of the human subject such that the axis guide extends perpendicular to a sagittal plane of the human subject.

13. A method for precise intra-operative positioning of a total hip prosthesis in a human subject, comprising:

determining a pelvic axis of a human subject in need of hip arthroplasty by placing an axis guide in contact with an anterior superior iliac spine (ASIS) on a left and a right side of the human subject such that the axis guide extends parallel to the pelvic axis;

driving two pins through apertures formed in the axis guide and into a pelvis of the human subject, wherein the two pins are placed perpendicular to the pelvic axis in at least one plane;

attaching a first electronic position sensor (ES1) to the two pins;

attaching a second electronic position sensor (ES2) to a cup impactor, wherein the first and second electronic position sensors are capable of acting in combination to report information useful to calculate a true angle of inclination and a true angle of forward flexion of an acetabular prosthetic cup;

contacting the cup impactor with an acetabular prosthetic cup that is to be implanted into a prosthetic implantation site in the subject;

transferring information from the first and second electronic position sensors to a computer processor running application software, wherein the application software calculates the true angle of inclination and the true angle of forward flexion of the acetabular prosthetic cup; and displaying results of the calculations on an electronic visual display device while the prosthesis is being surgically positioned for implantation into the subject.

14. The method of claim 13, wherein the calculated measurements are displayed on demand.

15. The method of claim 13, wherein the calculated measurements are displayed continuously.

16. The method of claim 13, further comprising attaching an electronic angle sensor to a structure selected from the group consisting of a native femoral neck, a prosthetic femoral stem, and a broach handle, wherein the electronic angle sensor is capable of reporting information useful to calculate an angle of anteversion of the structure to which it is attached; and transferring information from the electronic angle sensor to the computer processor running application software, wherein the application software calculates the angle of anteversion of the structure to which it is attached.

17. The method of claim 13, further comprising attaching an electronic leg length measurement unit, comprising (i) a reflection pin configured to be attached to a femur of the human subject; and (ii) an electronic distance sensor (DS) capable of being attached to a pelvis of the human subject and capable of reporting, to the computer processor, information about its distance from the reflection pin; and transferring information from the electronic distance sensor to the computer processor running the application software, wherein the application software calculates the distance between the distance sensor and the reflecting pin.

18. The method of claim 17, wherein the leg length measurement unit further comprises a substantially planar bracket constructed and arranged to receive at least two securing pins spaced and oriented in accordance with apertures of the axis guide; and wherein the electronic distance sensor (DS) is configured to be attached to the bracket.

\* \* \* \* \*